(12) United States Patent
He et al.

(10) Patent No.: US 6,669,956 B2
(45) Date of Patent: Dec. 30, 2003

(54) TABLETS INCORPORATING ISOFLAVONE PLANT EXTRACTS AND METHODS OF MANUFACTURING THEM

(75) Inventors: Min Michael He, Santa Clara, CA (US); Fang-Yu Liu, Fremont, CA (US); Joseph A. Fix, Half Moon Bay, CA (US); Martin Link, Sarasota, FL (US); Maria L. Kang, Belle Mead, NJ (US); Ezio Bombardelli, Viale Ortles 12 (IT)

(73) Assignees: Indena S.p.A., Milan (IT); Johnson & Johnson Consumer Companies, Inc., New Brunswick, NJ (US)

( * ) Notice: Subject to any disclaimer, the term of this patent is extended or adjusted under 35 U.S.C. 154(b) by 0 days.

(21) Appl. No.: 10/155,281

(22) Filed: May 23, 2002

(65) Prior Publication Data

US 2002/0182275 A1 Dec. 5, 2002

Related U.S. Application Data

(63) Continuation of application No. 09/273,237, filed on Mar. 18, 1999, now Pat. No. 6,413,546.

(51) Int. Cl.$^7$ ................................................. A61K 9/62
(52) U.S. Cl. .................... 424/464; 424/195.1; 424/474; 424/480; 424/725; 530/370; 530/377; 530/378
(58) Field of Search ............................. 424/195.1, 464, 424/474, 480, 725; 530/370, 377, 378

(56) References Cited

U.S. PATENT DOCUMENTS

| | | | |
|---|---|---|---|
| 5,674,548 A | 10/1997 | Nakamura et al. | 426/598 |
| 5,830,887 A | 11/1998 | Kelly | 514/182 |
| 5,855,892 A | 1/1999 | Potter et al. | 424/195.1 |
| 5,858,449 A | 1/1999 | Crank et al. | 426/656 |

FOREIGN PATENT DOCUMENTS

| | | | | |
|---|---|---|---|---|
| DE | 197 32 855 A1 | 2/1999 | | A61K/35/78 |
| DE | 197 32 866 A1 | 2/1999 | | A61K/35/78 |

OTHER PUBLICATIONS

Anthony, et. al.: "Effects of soy insoflavones on atherosclerosis: potential mechanisms[1–3]" *Am J Clin Nutr* 1998; (68) (suppl): 1390S–3S.

Greg Peterson and Stephen Barnes: "Genistein inhibition of the growth of human breast cancer cells: Independence from estrogen receptors and the multi–drug resistence gene" *Biochemical and Biophysical Research Communications* Aug. 30, 1991 vol. 179, No. 1, pp. (661–667).

Lee–Jane W Lu and Karl E. Anderson: "Sex and long–term soy diets affect the metabolism and excretion of soy isolflavones in humans [1–3]" *Am J Clin Nutr* 1998; (68) (suppl): 1500S–4S.

Zhang, et. al.: "Daidzein and Genistein Glucuronides in Vitro are weakly estrogenic and activate human natural killer cells at nutritionally relevant concentrations [1,2,3]" *J. Nutr.* 129: 399–405 (1999).

Mark Messina and Stephen Barnes: "The Role of Soy Products in Reducing Risk of Cancer [1]" *Journal of the National Cancer Institute* vol. 83, No. 8, 541–546 (Apr. 17, 1991).

Greg Peterson and Stephen Barnes: "Genistein and Biochanin A Inhibit the Growth of Human Prostate Cancer Cells but not Epidermal Growth Factor Receptor Tyrosine Autophosphorylation" *The Prostate* 22: 335–345 (1993).

Charland et. al.: "The effects of a soybean extract on tumor growth and metastasis" *International Journal of Molecular Medicine* 2: 225–228 (1998).

Kathleen A. Head , N.D. "Ipriflavone: An Important Bone–Building Isoflavone" *Alternative Medicine Review* vol. 4, No. 1, 10–22 (1999).

Derwent Publication Ltd., Lodon, GB, AN 1997–534403 XP002151122.

*Primary Examiner*—Thurman K. Page
*Assistant Examiner*—Konata M. George
(74) *Attorney, Agent, or Firm*—Townsend and Townsend and Crew LLP

(57) ABSTRACT

The invention is directed to novel tablets comprising isoflavone-containing plant extract and water-insoluble polysaccharides, and methods of manufacturing them.

20 Claims, No Drawings

TABLETS INCORPORATING ISOFLAVONE PLANT EXTRACTS AND METHODS OF MANUFACTURING THEM

The present application is a continuation of U.S. patent application Ser. No. 09/273,237, filed Mar. 18, 1999, and now U.S. Pat. No. 6,413,546 the disclosure of which is hereby incorporated by reference in its entirely for all purposes.

FIELD OF THE INVENTION

The invention is generally related to the fields of pharmaceuticals, compressed tablet formulations and methods of manufacturing tablets. In particular, the invention is directed to novel tablets comprising isoflavone-containing plant extract, particularly, extracts from fruits of plants from the Leguminosae family, and water-insoluble polysaccharides, and methods of manufacturing same.

BACKGROUND OF THE INVENTION

Isoflavones are naturally occurring glucosides found in many plants, particularly soybeans. As soybean is a rich protein source and soy is used as a dietary supplement, isoflavones are found in many foods and drinks. Isoflavone-containing soy proteins are used in the food industry to replace or extend meat, milk, egg, and other protein sources in traditional food products. One of the key factors limiting the use of soy protein concentrate, especially in nutritional beverages, milk replacers, and dairy products, is the soy taste present in the final product. Soy concentrates are also not widely used in nutritional beverages, milk replacers, and dairy products because of the presence of soy fiber as an insoluble component, causing an undesirable "mouthfeel." Administration of isoflavone-containing concentrates, as plant extracts, in the form of a tablet would eliminate undesirable "mouthfeel" and taste problems. However, isoflavone-containing plant extracts, because of their unique physiochemical properties, have not been reported to have been successfully formulated into a pressed tablet that can disintegrate in a reasonably short period of time. It has been a challenge to formulate isoflavone-containing plant extracts into pressed disintegratable tablets.

Even more significant than their use as a dietary supplement is the finding that isoflavones have many potential pharmaceutical uses. For example, isoflavones have been reported to be possible anti-cancer agents, see, e.g., Messina (1991) J. of the American Cancer Institute 83:542–545; Charland (1998) Int J Mol Med 2:225–228. Daidzein and genistein glucuronides, major isoflavone metabolites, may be partly responsible for the anti-cancer biological effects of isoflavones due to their estrogen receptor binding ability and natural killer (NK) cell activation, see, e.g., Zhang (1999) J Nutr 129:399–405; Lu (1998) Am. J Clin. Nutr. 68(6 Suppl):1500S-1504S. Soy genistein has been reported to be a chemopreventive agent against breast and prostate cancer in humans, see, e.g., Peterson (1991) Biochem. Biophysical Res. Com. 179:661–667; Peterson (1993) Prostate 22:335–345. Ipriflavone, an isoflavone synthesized from soy daidzein, is being tested to prevent and treat osteoporosis and other metabolic bone diseases, see, e.g., Head (1999) Altern. Med. Rev 4:10–22. Atherosclerosis was reduced in animals fed diets containing soy protein compared with those fed diets with animal protein; the components of soy protein that lower lipid concentrations are extractable by alcohol, i.e., they include the isoflavones genistein and daidzein (see, e.g., Anthony (1998) Am. J. Clin. Nutr. 68(6 Suppl):1390S-1393S.) It is also believed that daidzein and its metabolites, o-desmethylangolensin and dihydrodaidzein, are useful for altering the concentration of cholesterol constituents in the blood by increasing the concentration of high-density lipoprotein cholesterol and decreasing the concentration of low density lipoprotein cholesterol, see, e.g., Potter, et al., U.S. Pat. No. 5,855,892. However, to date it is not economical to administer these isoflavone components and metabolites in any purified form. Thus, the only economically practical means to administer these agents are as plant extracts, i.e., isoflavone-containing plant extracts, from, e.g., fruits of leguminous plants such as soybeans, red clover, Schigandra, and the like.

It would be preferable to administer plant extracts as compressed (solid) tablets for oral administration due to reasons of stability, economy, simplicity and convenience of dosing. However, most plant extracts (including isoflavone-containing plant extract), because of their unique physiochemical properties, are difficult to formulate into a compressed tablet form capable of dissolving in the stomach in a reasonably short period of time (e.g., a disintegration time at least about 30 minutes in gastric fluid). The difficulties in manufacturing plant extract-containing pressed tablet products are due to their physiochemical properties. The extracts contain fine particles that cause poor flow of the formulation and affects tablet compression.

Furthermore, the gel-forming nature of the plant extract makes it difficult to obtain a tablet with a reasonable disintegration time (e.g., at least about 30 minutes in gastric fluids). For example, soy plant extract, when exceeding 50% by weight in a tablet, tends to retard the disintegration time even in the presence of normally very efficient "superdisintegrants," such as croscarmellose sodium. It is the hygroscopicity of the plant extract that has impeded development of a one-tablet-per-dose formula using a direct compression approach.

Thus, there exists a great need for plant extract-containing compressed tablets with sufficient hardness to withstand packaging and handling, yet able to be administered orally, i.e., capable of dissolving in an aqueous environment similar to that found in the stomach (i.e., gastric juices) in a reasonable period of time (about 30 minutes or less). It would further be advantageous if such tablets could be made economically. The present invention fulfills these and other needs.

SUMMARY OF THE INVENTION

This invention provides for the first time pressed tablets comprising isoflavone-containing plant extracts, and methods of manufacturing them, that have advantageous physical-chemical properties and are economical to produce.

The invention provides physiologically acceptable tablets comprising an isoflavone-containing plant extract and a compressed tablet formulation that comprises a water-insoluble polysaccharide, wherein the amount of the water-insoluble polysaccharide in the tablet comprises at least about 15% of the dry weight of the tablet. In alternative embodiments, the water-insoluble polysaccharide is a plant water-insoluble polysaccharide, the plant water-insoluble polysaccharide is a soybean plant water-insoluble polysaccharide, and the soybean plant water-insoluble polysaccharide is Emcosoy® polysaccharide. In one embodiment, the isoflavone-containing plant extract is from the fruit of a plant from the Leguminosae family, and, in a preferred embodiment, a soy bean extract.

In alternative embodiments, the water-insoluble polysaccharide in the invention's tablets comprise between about 15% to about 25% of the dry weight of the tablet; and between about 21% to 22% of the dry weight of the tablet.

In other embodiments, the amount of the isoflavone-containing plant extract in the tablets comprise between about 10% to about 85%, about 20% to about 75%, about 30% to about 70%, and about 45% to about 65% of the dry weight of the tablet.

In one embodiment, the tablets can dissolve in a gastric fluid within at least about 30 minutes; in a preferred embodiment, the tablets can dissolve in less than about 15 to 16 minutes.

The tablets of the invention can further comprise a micronized fatty acid, which, in alternative embodiments, is present in the tablet at amounts between about 1% to about 5% of the dry weight of the tablet, and, about 2% of the dry weight of the tablet. The tablets of the invention can further comprise a silica gel, which, in alternative embodiments, is in an amount between about 1% to about 5% of the dry weight of the tablet, and, about 2% of the dry weight of the tablet. In a preferred embodiment, the micronized fatty acid is a micronized stearic acid.

In various embodiments, the tablets of the invention are suitable for delivery to a body cavity, including the oral, buccal or sublingual cavities, and swallowing. The tablet formulations of the invention can further comprise at least one additive agent, including, e.g., a disintegrant, a flavorant, an artificial sweetener, a perfume, and a colorant.

The invention also provides tablets made by a direct compression ("dry blend") process comprising the following steps: (a) mixing an initial formulation comprising an isoflavone-containing plant extract, a water-insoluble polysaccharide (e.g., Emcosoy® polysaccharide), wherein the amount of the water-insoluble polysaccharide in the tablet comprises at least about 15% of the dry weight of the tablet, a filler, and, a silica gel glidant, wherein the amount of the silica gel in the tablet comprises between about 1% to about 5% of the dry weight of the tablet; (b) milling the mixed formulation; (c) mixing into the milled and mixed formulation a micronized fatty acid (e.g., a micronized stearic acid), wherein the amount of the micronized fatty acid in the tablet comprises between about 1% to about 5% of the dry weight of the tablet; and, (d) pressing the milled formulation into a tablet form, wherein the compression force of the press on the tablet is at least about 15 kilopounds. In alternative embodiments, in the dry blend process, the compression force of the press on the tablet is between about 15 to about 30 kilopounds, and between about 17 to about 23 kilopounds. In these tablets, the isoflavone-containing plant extract can be an extract from the fruit of a Leguminosae family plant, e.g., a soy plant bean.

The tablets of invention manufactured by the dry blend process can further comprise a coating made by: (a) coating the pressed tablets with an aqueous dispersion comprising a cellulose-based polymer; (b) drying the coated tablets, wherein the drying does not heat the tablet more than up to about 40° C.

The invention also provides tablets made by a granulation process comprising the following steps: (a) mixing an initial formulation comprising an isoflavone-containing plant extract and a water-insoluble polysaccharide (e.g., Emcosoy® polysaccharide), wherein the amount of the water-insoluble polysaccharide in the tablet comprises at least about 15% of the dry weight of the tablet; (b) granulating the mixed formulation using an aqueous solution comprising at least about 0.5% cellulose-based polymer; (c) drying the granulated formulation; and (d) pressing the dried, granulated formulation into a tablet form. In these tablets of the invention, the isoflavone-containing plant extract can be an extract from the fruit of a Leguminosae family plant, e.g., soy bean.

The tablets of the invention manufactured by the granulation process can further comprise a coating made by (a) coating the pressed tablets with an aqueous dispersion comprising a cellulose-based polymer; (b) drying the coated tablets, wherein the drying does not heat the tablet more than about 40° C.

The invention also provides a direct compression ("dry blend") process for producing a tablet comprising the following steps: (a) mixing an initial formulation comprising an isoflavone-containing plant extract, a water-insoluble polysaccharide (e.g., Emcosoy® polysaccharide), wherein the amount of the water-insoluble polysaccharide in the tablet comprises at least about 15% of the dry weight of the tablet, a filler, and a silica gel glidant wherein the amount of the silica gel in the tablet comprises between about 1% to about 5% of the dry weight of the tablet; (b) milling the mixed formulation; (c) mixing into the milled and mixed formulation a micronized fatty acid (e.g., a micronized stearic acid), wherein the amount of the micronized fatty acid in the tablet comprises between about 1% to about 5% of the dry weight of the table; and, (d) pressing the milled formulation into a tablet form, wherein the compression force of the press on the tablet is at least about 15 kilopounds. In this process, the isoflavone-containing plant extract can be from the fruit of a Leguminosae family plant, such as a soy bean extract. In one embodiment in this process, the compression force of the press on the tablet is between about 17 to about 23 kilopounds.

This dry blend process can further comprises a coating process comprising the following steps: (a) coating the pressed tablets with an aqueous dispersion comprising a cellulose-based polymer; (b) drying the coated tablets, wherein the drying does not heat the tablet more than about 40° C.

The invention further provides a granulation process for producing a tablet comprising the following steps: (a) mixing an initial formulation comprising an isoflavone-containing plant extract and a water-insoluble polysaccharide (e.g., Emcosoy® polysaccharide), wherein the amount of the water-insoluble polysaccharide in the tablet comprises at least about 15% of the dry weight of the tablet; (b) granulating the mixed formulation using an aqueous solution comprising at least 0.5% cellulose-based polymer; (c) drying the granulated formulation; and (d) pressing the dried, granulated formulation into a tablet form.

This granulation process can further comprise a coating process comprising the following steps: (a) coating the pressed tablets with an aqueous dispersion comprising a cellulose-based polymer; (b) drying the coated tablets, wherein the drying does not heat the tablet more than about 40° C.

The invention also provides a physiologically acceptable tablet comprising a compressed tablet formulation that comprises an isoflavone-containing plant extract, wherein the amount of the isoflavone-containing plant extract in the tablet comprises about 45% to about 65% of the dry weight of the tablet; a filler, a micronized fatty acid (e.g., a micronized stearic acid), wherein the amount of the micronized fatty acid in the tablet comprises between about 1% to about 5% of the dry weight of the tablet; a silica gel glidant, wherein the amount of the silica gel in the tablet comprises between about 1% to about 5% of the dry weight of the tablet; a water-insoluble polysaccharide (e.g., Emcosoy® polysaccharide), wherein the amount of the water-insoluble polysaccharide in the tablet comprises at least about 15% of the dry weight of the tablet, and wherein the tablet can substantially dissolve in a gastric fluid in, in alternative embodiments, at least about 15 minutes and at least about 30 minutes.

A further understanding of the nature and advantages of the present invention may be realized by reference to the remaining portions of the specification, the figures and claims.

All publications, patents and patent applications cited herein are hereby expressly incorporated by reference for all purposes.

DETAILED DESCRIPTION OF THE INVENTION

The present invention provides for novel pharmaceutically acceptable tablets. Also provided are methods of making such tablets. The invention provides new formulations and manufacturing processes that overcome the problems that had previously prevented the formulation of isoflavone-containing plant extract into a pressed tablet, while at the same time achieving the optimal balance between the physical properties needed for manufacturing and handling, e.g., hardness, and the tablet's disintegration characteristics (particularly, in the gastric fluid of the stomach), in addition to other advantageous properties.

The invention uses water-insoluble polysaccharides (e.g., Emcosoy®) at high usage levels (about 22% by weight) in the manufacturing processes of isoflavone plant extract containing tablets. In one embodiment, pressed tablets with a disintegration time of less than 16 min. are manufactured. This amount of water-insoluble polysaccharide is novel to the invention, as it is greater than accepted manufacturing practice (the supplier-recommended usage level for Emcosoy® soy polysaccharides in tablets is only 4% to 10%).

Definitions

The term "artificial sweetener" as used herein incorporates the term's common usage and refers to any synthetic composition that sweetens the taste of a formulation.

The term "cellulose based polymer" refers to any polymeric cellulose, synthetic or derived or isolated from a natural source, such as, e.g., , hydroxypropyl cellulose; hydroxypropylmethyl cellulose; hydroxyethyl cellulose; methyl cellulose; cellulose acetate; or other cellulose based water soluble polymers.

The term "coating" refers to any material or composition added to the core tablet. For example, in one embodiment, a coating is added to the pressed "core" tablets of the invention by spraying the tablet with an aqueous dispersion comprising a cellulose based polymer.

The term "colorant" as used herein incorporates the term's common usage and refers to any composition that adds color to a formulation, including the core tablet or the coating.

The terms "compressing," "pressing," "molding" and "press molding" refer to the process of applying compressive force to a formulation (powder or granules), as within a die, to form a tablet. The terms "compressed tablet" and "pressed tablet" mean any tablet formed by such a process.

The term "drying" and "dried" refer to a process which decreases the water content of a composition, as the drying of a humidified tablet. The term "dried tablet" refers to a tablet that has been treated in any manner to decrease the amount of water in the formulation. For example, in one embodiment, the formulation of the invention is manufactured into tablet form using a granulation process, and a tablet is dried after its initial granulation and compression into a tablet form. In another embodiment, pressed "core" tablets of the invention are coated with an aqueous dispersion, which is subsequently dried.

The term "dry weight" as used herein incorporates the its common usage and, in the context of the tablets of the instant invention, means the weight of a tablet after substantially all the water (or other solution or solvent) has been removed from the tablet.

The term "formulation" refers to any mixture of compositions used to make the tablets of the invention, including both core tablet and coating material.

The term "disintegrant" as used herein incorporates the term's common usage and refers to any composition which decreases the disintegration time (accelerates the rate of disintegration) of a tablet.

The term "filler" as used herein incorporates the term's common usage and refers to any inert material or composition added to a formulation to add bulk.

The term "flavorant" as used herein incorporates the term's common usage and refers to any composition which adds flavor to or masks the bad taste or smell of a formulation.

The term "gastric fluid" as used herein means any fluid have substantially the same properties as fluids found in the stomach, including "simulated" gastric fluid, as described below.

The term "granulating" refers to the process of blending and mixing a formulation in an aqueous solution, as described infra.

The term "isoflavone-containing plant extract" as used herein incorporates the term's common usage and refers to naturally derived isoflavone-containing plant extracts and comparable synthetic isoflavone-containing compositions. Isoflavone-containing plant extracts are typically derived as natural products from plants, e.g., fruits of plants from the Leguminosae family (i.e., fruits of leguminous plants), such as the soy bean, see, e.g., Crank, et al., U.S. Pat. No. 5,858,449. The term includes relatively crude plant extracts containing isoflavone and relatively purified and isolated components thereof, including all isoflavone glycoside components, as described in further detail below. In one embodiment, fruits of the Leguminosae family, particularly soy beans, are a preferred source of isoflavone plant extract.

The terms "leguminous plant" and "plant of the Leguminosae family" incorporate their common usage, such as detailed herein, infra.

The terms "micronized fatty acid" and "micronized stearic acid" refers to a fatty acid powder and a stearic acid powder, respectively, where more than about 90% of the particles in the powder have a particle size of less than about 30 to 50 microns (for example, they are both fatty acid powders which have been passed through a #325 mesh screen). In one embodiment, the micronized stearic acid is the commercially available Tri Star, NF (Sego International, Inc., Portland, Oreg.).

The term "perfume" refers to any composition that contributes to the odor or taste, or masks an unpleasant smell, of a formulation.

The term "physiologically acceptable" refers to any combination of materials or compositions that are not harmful, i.e., non-toxic, to cells and tissues under physiologic (in vivo) conditions.

The term "polysaccharide" refers to any polysaccharide, or derivative thereof, from any natural or synthetic sources. The term "water-insoluble polysaccharide" refers to a polysaccharide polymeric composition insoluble in an aqueous solution. For example, in one embodiment, the water insoluble polysaccharide is the commercially available Emcosoy® polysaccharide (Penwest Pharmaceuticals, Co., (formerly Mendell), Patterson, N.Y.).

The term "silica gel" as used herein means a glidant which conforms to the specifications for Silicon Dioxide contained in the United States Pharmacopeia/National Formulary (USP/NF) and the Food Chemical Codex (FCC).

The term "soy plant" or "soybean plant" means any plant from the Leguminosae family, e.g., Glycine max.

The term "tablet" is used in its common context, and refers to a solid composition made by compressing and/or molding a mixture of compositions in a form convenient for swallowing or application to any body cavity.

Isoflavone-Containing Plant Extracts

In nature, isoflavone-containing plants primarily are legumes, clovers, the root of the kudzu vine (pueraria root), and Schigandra. Isoflavone-containing plants appear to be widely distributed in the plant kingdom. Over 700 different isoflavones have been described. However, the most common source of isoflavone plant extract is from the fruits (e.g., beans, peas) of the Leguminosae family, including, e.g., soy beans and chick peas. Clover sources of isoflavone plant extract include red clover and subterranean clover. In one embodiment, fruits of the Leguminosae family, particularly soy beans, are a preferred source of isoflavone plant extract.

In raw plant material, isoflavones occur principally as glycosides. The isoflavones in vegetable protein whey include isoflavone glucosides (glucones), isoflavone conjugates, and aglucone isoflavones. Isoflavone glucosides have a glucose molecule attached to the isoflavone moiety of the compound. Isoflavone conjugates have additional moieties attached to the glucose molecule, for example, 6"-OAc genistin contains an acetate group attached to the six position of the glucose molecule. Aglucone isoflavones consist of an isoflavone moiety without an attached glucose molecule. Soy whey contains three "families" of isoflavone compounds having corresponding glucoside, conjugate, and aglucone members: the genistein family, the daidzein family, and the glycitein family. The genistein family includes the glucoside genistin; the conjugates 6"-OMal genistin (6"-malonate ester of genistin) and 6"-OAc genistin (6"-acetate ester of genistin); and the aglucone genistein. The daidzein family includes the glucoside daidzin; the conjugates 6"-OMal daidzin, and 6"-OAc daidzin; and the aglucone daidzein. The glycitein family includes the glucoside glycitin, the conjugate 6"-OMal glycitin, and the aglucone glycitein.

Isoflavone-containing plant extract can be made from any leguminous plants in addition to the soybean plant (*Glycine max*), such as, e.g., Indian liquorice (*Abrus precatorius*); various species of Acacia spp. including, *A. aneura, A. cibaria, A. longifolia,* and *A. oswaldii;* ground nut (*Apio tuberosa*); ground pea (*Arachis hypogea*); milk vetch (*Astragalus edulis*); marama bean (*Bauhinia esculenta*); sword bean (*Cajanus cajan indicus*); jack bean (*Canavalia ensiformis*); sword bean (*Canavalia gladiata*); seaside sword bean (*Canavalia rosea*); various Cassia spp. including *C. floribunda, C. laevigata,* and *C. occidentalis;* carobbean (*Ceratonia siliqua*); chick pea (*Cicer arietinum*); yebnut (*Cordeauxia edulis*); various Crotalaria spp. including *C. laburnifolia,* and *C. pallida;* cluster bean (*Cyamopsis psoralioides*); tallow tree (*Detariaum senegalense*); sword bean (*Entada scandens*); balu (*Erythrina edulis*); inga (Ingaedulis); Polynesian chestnut (*Inocarpus fagifer*); hyacinth bean (*Lablab purpureus*); grass pea or Indian vetch (*Lathyrus sativus*); cyprus vetch (*Lathyrus ochrus*); lentil (*Lens culinaris*); jumping bean (*Leucaenal eucocephala*); various Lupinus spp. including *L. albus, L. luteus, L. angustifolium, L. mutabilis,* and *L. cosentinii;* ground bean (*Macotylma geocarpa*); horse gram (*Macrotyloma uniflorum*); alfalfa (*Medicago sativa*); velvet bean (*Mucuna pruriens*); yam beans (*Pachyrhyzus erosus, P. tuberosus*); African locust bean (*Parkia clappertoniana*); *Parkia speciosa;* oil bean tree (*Pentaclethra macrophylla*); various Phaseolus spp. including *P. acutifolius, P. vulgaris, P. luntus, P. coccineus, P. adenathus, P. angulris, P. aureus, P. calcaratus, P. mungo,* and *P. polystachyus;* garden pea (*Pisum sativum*); djenko bean (*Pithecolobium lobatum*); mesquite (various Prosopis spp.); goa bean (*Psophocarpus scandens, P. tetragonolobus*); various Psoralea spp.; *Sesbania bispinosa;* yam bean (*Sphenostylis stenocarpa*); tamarind (*Tamarindus indica*); fenugreek (*Trigonella foenumgraecum*); vetches (various Vivia spp. including *V. sativa, V. atropurpurea, V. ervilia,* and *V. monantha*); broad bean (*Vicia faba*); black gram (*Vigna mungo*); various Vigna spp. including *V. radiata, V. aconitifolia, V. adanatha, V. angularus, V. tribolata, V. umbelata,* and *V. unguiculata;* and, earth pea (*Voandzeia subterranea*).

Isoflavone-containing plant extract can be processes and isolated from any plant source in which it naturally occurs. For example, isoflavones may be isolated from red clover as disclosed by e.g., Wong (1962) J. ScL. Food Agr., Vol. 13, p. 304. Isoflavones may be isolated from soybean as described by, e.g., Potter, et al., U.S. Pat. No. 5,855,892; Shen, et al.; U.S. Pat. No. 5,851,792; Kelly, et al. U.S. Pat. No. 5,830,887; Waggle, et al., U.S. Pat. No. 5,821,361. Isoflavones may be isolated from molds, e.g., from *Micromonospora halophytica* (see, e.g., Ganguly (1970) Chem. & Ind. (London), p. 201).

Alternatively, isoflavones can be synthetically prepared, see, e.g., Baker et al, J Chem. Soc., p. 274 (1933); Wesley et al., Ber. Vol. 66, p. 685 (1933); Mahal et al., J. Chem. Soc., p. 1769 (1934); Baker et al., J. Chem. Soc., p. 1852 (1953); Farkas, Ber. Vol. 90, p. 2940 (1957), and Potter, et al., U.S. Pat. No. 5,855,892. A process for converting isoflavone glucosides to aglucone isoflavones in a vegetable protein whey is described in PCT/US/94/10699. See also, Kanaoka, et al., U.S. Pat. No. 5,847,108.

Isoflavones and isoflavone-containing plant extracts are also commercially available. Soy plant-derived material from which isoflavone can be isolated include, e.g., soy beans, dehulled soy beans, soy meal, soy flour, soy grits, soy flakes (full fat and defatted), soy molasses, soy protein concentrate, soy whey, soy whey protein, and soy protein isolate. Isoflavones can be extracted from any of these soy materials with a low molecular weight organic extractant, e.g., an alcohol (e.g., aqueous ethyl alcohol or methyl alcohol), ethyl acetate, acetone, or ether. The extractant can have a pH of about the isoelectric point of soy protein (about pH 4 to pH 5) to minimize the amount of soy protein extracted by the extractant. The extractant containing the isoflavones can be further separated from insoluble soy materials to form an isoflavone enriched extract. Impurities in the extract can be separated out by contacting the extract with a material which adsorbs the isoflavones in the extract, and eluting the adsorbed isoflavones out of the adsorbent material with a solvent which causes the isoflavones to be differentially eluted from the adsorbent material.

Tablet Formulation

The invention provides a physiologically acceptable compressed tablet comprising a formulation that includes an isoflavone-containing plant extract, particularly, an extract from the fruit of a leguminous plant, and a water-insoluble polysaccharide, where the amount of the water-insoluble polysaccharide in the tablet comprises at least about 15% of the dry weight of the tablet. In alternative embodiments, the tablet can also contain micronized fatty acid, fillers, and/or glidants (e.g., silica gel glidants).

Water Insoluble Polysaccharides

For the first time the invention provides tablets and methods of manufacturing them using water-insoluble polysaccharides. Use of the water-insoluble polysaccharide solves a long-felt need to formulate isoflavone-containing plant extracts into a pressed tablet form that has sufficient hardness to be packaged and handled by the consumer and yet still be able to disintegrate in an aqueous solution (e.g., a body fluid, such as gastric fluid) within 30 minutes after being used (e.g., swallowed). Without the water-insoluble polysaccharide, the pressed tablet would not be able to disintegrate in less than 30 minutes after exposure to the aqueous solution. In fact, manufacturers of water-insoluble polysaccharides (e.g., Penwest Pharmaceuticals, Co., Patterson, N.Y.) recommend that the amount of soy polysaccharide (the water-insoluble polysaccharide used in a preferred embodiment of the invention) used in making a tablet should be between 4% to 10%. However, this would result in a pressed core tablet with unacceptable properties (i.e., a tablet that could not disintegrate in less than 30 minutes in an aqueous solution). In summary, the invention's first use of water-insoluble polysaccharide at higher concentrations than were considered standard manufacturing practice solves a problem seen in the manufacturing and use of isoflavone plant extract-containing pressed tablets. Thus, the tablets and methods of the invention differ from recommended manufacturing practices.

Water-insoluble polysaccharides can be isolated from any source. A common and economical source is soy. Water-insoluble polysaccharides are commonly derived from soy as insoluble dietary fiber, see, e.g., Fredstrom (1991) *JPEN J Parenter. Enteral Nutr.* 15:450–453. Water-insoluble polysaccharides are also commercially available, and may be purchased, e.g., from Penwest Pharmaceuticals, Co., Patterson, N.Y., as the product Emcosoy® soy polysaccharide.

One skilled in the art using routine and well-known methods can readily determine whether any polysaccharide has the required property of being "water-insoluble" and thus, useful in the manufacture of the tablets of the invention.

Other Formulation Components

Lubricants help in the manufacturing of a tablet; e.g., they help prevent "ejection sticking" of compressed formulation to the pressing dies and punches. "Ejection sticking" is a particularly difficult problem when a formulation comprising isoflavone-containing plant extract is pressed into tablets by the dry blend process (discussed in further detail below). This difficulty is for the first time overcome by the invention's use of micronized fatty acid, such as a micronized stearic acid. In one embodiment, the amount of the micronized fatty acid in the tablet comprises between about 1% to about 5% of the dry weight of the tablet.

Furthermore, without use of micronized fatty acids, use of an isoflavone-containing plant extract in a pressed tablet formulation will result in unacceptable blistering, cracking or delamination of the final product. The problems of blistering, cracking and delamination were solved by using silica gel, micronized stearic acid and the multiple milling process of the invention.

In an alternative embodiment, the tablets of the invention can optionally include additional lubricants, such as the insoluble lubricant magnesium stearate, or a derivative thereof. The magnesium stearate can be between 0.1% and 2.0%, or between 0.5% and 1.0%, of the weight of the tablet.

In another embodiment, disintegrants are also included in the formulations of the invention. For example, non-saccharide water soluble polymers, such as cross-linked povidine, can be added to the formulation to further enhance the rate of disintegration. Other disintegrants than can also be used include, e.g., croscarmellose sodium, sodium starch glycolate, and the like; see, e.g., Khattab (1992) J. Pharm. Pharmacol. 45:687–691.

The tablets of the invention can further comprise any medicament, drug, palliative, nutritive, or pharmaceutically active material, e.g., a drug, medicament, nutrient, placebo, and the like. However, the invention is broadly applicable to a wide variety of isoflavone plant extract-containing tablets for uses in addition to those discussed above (e.g., anti-cancer, atherosclerosis, dietary supplement), including, but not limited to, tablets for, e.g., antacids, gastrointestinal agents, analgesics, antiinfectives, CNS-active agents, cardiovascular agents, cough therapies, vitamins, and other pharmaceutical, nutritional and dietary agents.

Any colorant can be used, as long as it is approved and certified by the FDA. For example, exemplary colors include allura red, acid fuschin D, naphtalone red B, food orange 8, eosin Y, phyloxine B, erythrosine, natural red 4, carmine, to name a few. The most common method of adding color to a tablet formulation is to dissolve the dye in solution prior to the granulating process.

Sweetening agents can be added to the tablet formulation (in the core tablet and/or just the coating solution) to create or add to the sweetness. Saccharide fillers and binders, e.g., mannitol, lactose, and the like, can add to this effect. For example, cyclamates, saccharin, aspartame, acesulfame K (Mukherjee (1997) Food Chem. Toxicol. 35:1177–1179), or the like (Rolls (1991) Am. J. Clin. Nutr. 53:872–878), can be used. Sweeteners other than sugars have the advantage of reducing the bulk volume of the tablet (core tablet and/or coat) and not effecting the physical properties of the tablet.

Manufacturing Processes

The invention provides for methods of manufacturing the isoflavone plant extract-containing tablets of the invention. In preferred embodiments, the tablets are manufactured by a direct compression process and a granulation process. Both of these processes generate a "core tablet." which can, in an alternative embodiment, be further processed to add a "coating" which can contain, e.g., cellulose-based polymers, coloring agents, flavorants, and the like.

The Direct Compression Process of Manufacture

The steps involved in the manufacture of an isoflavone plant extract-containing "core tablet" by a direct compression, or "dry blend," process comprise a mixing (blending) step, a milling step (and in one embodiment, a second mixing step), and a pressing step. In one embodiment, the core tablet is further processed and a "coating" is added in a two-step process; a coating step and a drying step. All of these processing steps require no more than conventional processing and manufacturing equipment.

Mixing Step

In the direct compression ("dry blend") manufacturing process, an initial formulation of components of the tablet, including an isoflavone-containing plant extract and a water-insoluble polysaccharide (in an amount resulting in it being at least 15% of the dry weight of the tablet), are mixed. In alternative embodiments, a micronized fatty acid is added in this initial formulation, or, after the milling step, or both. In either case, the amount of micronized fatty acid added to the formulation is sufficient to ensure that it will comprise between about 1% to about 5% of the dry weight of the tablet. Isoflavone plant extract-containing formulations which use conventional lubricant(s) in place of micronized fatty acid cannot be pressed into tablet forms in a dry blend compression process without significant "sticking" problems, i.e., the formulation sticking on the press punches. This problem is particularly acute when rotary tablet presses are used.

In one embodiment, a filler (e.g., microcrystalline cellulose), a glidant (e.g., a silica gel), or both are added to the initial formulation before or during mixing. Alternatively, either or both (filler or glidant) can be added after milling. The amount of silica gel added to the tablet is sufficient to ensure that it will comprise between about 1% to about 5% of the dry weight of the tablet.

In other embodiments, either before or after milling, additional components can be added to the formulation, e.g., a filler (such as microcrystalline cellulose) or glyceryl behenate. Glyceryl behenate reduces problems such as capping, sticking or delamination associated with the use of other lubricants (e.g., regular grade stearic acid, magnesium stearate) in a similar formulation. However, glycerol behenate cannot replace micronized fatty acid to prevent isoflavone plant extract-containing formulations from sticking on tablet press punches (as discussed above). In one embodiment, the formulation is mixed with about 13 to about 15 parts (by weight) of microcrystalline cellulose and one to two parts glyceryl behenate.

Milling Step

The initial formulation, after mixing, is milled using conventional techniques and machinery. In alternative embodiments, the initial formulation mixture is milled through a 20-mesh and a 30-mesh screen using commercially available milling equipment such as, e.g., Quadro® or Comil® (Quadro, Millburn, N.J.).

Compression, or "Pressing," Step

The pressing or compression of the formulation after the milling step and, in some embodiments, after an additional mixing step, can be accomplished using any tablet press. Many alternative means to effect this step are available, and the invention is not limited by the use of any particular equipment. In a preferred embodiment, the compression step is carried out using a rotary type tablet press. The rotary type tableting machine has a rotary board with multiple through-holes, or dies, for forming tablets. The formulation is inserted into the die and is subsequently press-molded.

The diameter and shape of the tablet depends on the die and punches selected for the compression of the milled and mixed formulation. Tablets can be discoid, oval, oblong, round, cylindrical, triangular, and the like. The tablets may be scored to facilitate breaking. The top or lower surface can be embossed or debossed with a symbol or letters.

The compression force can be selected based on the type/model of press, what physical properties are desired for the tablets product (e.g., desired, hardness, friability, in vivo disintegration or dissolution characteristics, etc.), the desired tablet appearance and size, and the like. In a preferred embodiment, the compression force of the press on the tablet is at least about 15 kilopounds (Kp). The "core" tablets from the compression stage typically have a hardness of about 5 Kp to about 25 Kp, with preferred embodiments having a hardness of about 11 Kp to about 19 Kp. In other embodiments, the tablet can dissolve in a gastric fluid within at least about 30 minutes and at least about 15 minutes.

The Granulation Process of Manufacture

The steps involved in the manufacture of a isoflavone plant extract-containing "core tablet" by a granulation process comprise a mixing (blending) step, a granulation step, a drying step, and a compression (or "pressing") step. In one embodiment, the core tablet is further processed and a "coating" is added in a two-step process; a coating step and a drying step. All of these processing steps require no more than conventional processing and manufacturing equipment.

Granulation Step

In the granulation manufacturing process, an initial formulation of components of the tablet, including an isoflavone-containing plant extract and a water-insoluble polysaccharide (in an amount resulting in it being at least 15% of the dry weight of the tablet), are mixed. This initial mixture is then blended, or "granulated," in an aqueous solution comprising at least about 0.5% cellulose-based polymer. This blending process is commonly called "wet granulation." "Granulation" is commonly defined as a size-enlargement process in which small particles are gathered into larger, permanent aggregates in which the original particles can still be identified. "Wet granulation" is a variation on this process, as refers to a granulation that adds solvents and binders to the enlargement process. See, e.g., Lipps (1993) J. Pharm. Sci. 83:937–947; Olmo (1998) Drug Dev. Ind. Pharm. 24:771–778.

A variety of such blending, or mixing, or granulating, apparatus are commonly available. For example, the granulation can be done on a Fluid Bed Granulator, such as the one designed by Glatt Air Techniques Inc., N.J.

The temperature during granulation can be set at any point as long as it does not exceed the melting point of any components in the formulation and the balance between spraying and drying is kept. However, in a preferred embodiment, the temperature during granulation (and drying) is at a relatively low heat setting, i.e., a range of about 20° C. to about 50° C. The formulation, once granulated, is dried until the temperature reaches 40° C. before pressing into a tablet form.

Sieving and Further Mixing Steps

In other embodiments of the granulation manufacturing process, the granulated formulation is sieved through a #20 mesh screen and a #30 mesh screen.

In another embodiment, after sieving, or, if the granulated formulation is not sieved, after the granulation step, additional components can be added to the formulation, e.g., a filler (such as microcrystalline cellulose) or glyceryl behenate. In one embodiment, the formulation is mixed with about 15 parts (by weight) of microcrystalline cellulose, and, optionally, one part glyceryl behenate. In another embodiment, either or both (the cellulose or behenate) are added in the initial mixing step.

In alternative embodiments, in addition to or in place of hydroxypropyl methyl cellulose, other hydrophilic polymers which provide a binding effect in granulation can also be used, e.g., polyvinyl pyrrolidone (PVP) or derivatives, polyvinyl alcohol, or hydroxypropyl cellulose of pharmaceutical grade. The glyceryl behenate may be replaced by other pharmaceutical lubricants such as, e.g., magnesium stearate, stearic acid, or other hydrogenated vegetable oil or triglycerides.

Compression, or "Pressing," Step

The pressing or compression of the formulation after the granulation step can be accomplished using any tablet press.

Many alternative means to effect this step are available, and the invention is not limited by the use of any particular apparatus. In a preferred embodiment, the compression step is carried out using a rotary type tablet press using standard manufacturing procedures, as generally described above (for the direct compression, "dry blend," process).

Coating Core Tablets

In alternative embodiments, core tablets of the invention made by both the granulation and direct compression manufacturing processes are further treated to generate a tablet "coat." The coating process of the invention includes the steps of coating the pressed tablets with an aqueous dispersion comprising a cellulose-based polymer; followed by drying the coated tablets, where the drying does not heat the tablet more than about 40° C.

As discussed above, the coating solution can contain a variety of ingredients, including flavorants, colorants, and the like. For example, in one embodiment, the core tablet is coated with an aqueous dispersion of hydroxypropyl methylcellulose, polyethylene glycol, titanium dioxide, and a colorant. In another exemplary embodiment, the core tablet is coated with an aqueous dispersion of hydroxypropyl methylcellulose, polyethylene glycol, and maltodextrin.

Standard manufacturing techniques and equipment are used in the coating process; see, e.g., Sastry (1998) Pharm Dev Technol. 3:423–432; Parikh (1993) Pharm Res. 10:525–534.

Measuring Tablet Properties

The manufacturing methods of the invention produce a novel tablet capable of disintegrating in a body cavity, e.g., as when taken orally (to dissolve in the gastric fluid) or to be used as a "lozenge" to dissolve in the mouth; when placed onto a mucous membrane, as in the buccal space or sublingually; intravaginally; intrarectally; and the like.

The superior qualities (physical properties) of the tablet of the invention can be measured, and such measurements can be used, e.g., for quality control, to compare to tablets manufactured by other processes. Physical properties can be measured using a variety of conventional assays and tests well described in the patent, pharmaceutical and scientific literature. See, e.g., Kopp (1989) J. Pharm. Pharmacol. 41:79–82. A few exemplary tests are set forth below, including means to measure tablet hardness, friability, disintegration time, dissolution time, wetting time, and porosity.

Tablet Hardness: "Crushing," or "Tensile" Strength

Tablet hardness is physical strength measurement of the tablet. The resistance of a tablet to chipping, abrasion, or breakage under conditions of storage, transportation and handling before usage depends on its hardness, or "crushing strength." The tablet "crushing" or "tensile" strength is defined as the force required to break a tablet by compression in the radial direction. It is typically measured using one of the many commonly available tablet hardness testers. For example, "Stokes" and "Monsanto" hardness testers measure the force required to break the tablet when the force generated by a coil spring is applied diametrically to the tablet. A "Strong-Cobb" hardness tester also measures the diametrically applied force required to break a tablet, the force applied by an air pump forcing a plunger against the tablet placed on an anvil. Electrically operated hardness testers, such as the Schleuniger apparatus (also known as a "Heberlein") can be used. See also, TS-50N, Okada Seiko Co., Japan; Bi (1996) Chem. Pharm. Bull. (Tokyo) 44:2121–2127.

Friability

Tablet friability is a physical strength measurement of a tablet, and is defined as the ability of the compressed tablet to resist abrasion and attrition. It is typically measured by turning tablets in a rotating vessel and determining weight loss (see De Jong (1987) Pharm Weekbl (Sci) 9:24–28). These rotating devices are called "friabilators." The friabilator provides frictional abrasion to the tablet sample and is used to measure the resistance to abrasion or attrition of tablets. The loss of weight is measured after a fixed number of revolutions of a drum rotating at a controlled rate.

Friabilator apparatus typically use a 285 mm drum of transparent synthetic polymer with polished internal surfaces. One side of the drum is removable. The tablets are tumbled at each turn of the drum by a curved projection that extends from the middle of the drum to the outer wall. The drum is attached to the horizontal axis of a device that rotates at about 25 to 30 rpm. Thus, at each turn, the tablets roll or slide and fall onto the drum wall or onto each other. Many such apparatus are commonly available, e.g., the Roche type friabilator (Van Kel Industries, Inc., Edison, N.J.); a Erweka Friability Apparatus (Erweka Instruments, Milford, Conn.) (Bi (1996) supra, Chowhan (1982) J. of Pharm. Sci. 71:1371–1375), and the like.

In one exemplary protocol, the standard United States Pharmacopia (USP) protocol for measuring friability is used. Briefly, the tablets are placed in a friabilator that is a 285 mm drum, about 39 mm in depth, of transparent synthetic polymer. The tablets are "tumbled" at each turn of the drum by a curved projection that extends from the middle of the drum. The drum is rotated for about four minutes at about 25 rpm, resulting in a total of 100 rotations. A minimum of about 20 tablets are used in any test, unless the tablets weigh over 650 mg, in which case only 10 tablets are used. After the allotted time, the tablets are removed from the friabilator, and, with the aid of air pressure or a brush, adhering particles and dust are removed, and remaining tablets are accurately weighed. Percent loss of weight is calculated.

Measuring Disintegration Times

In measuring the disintegration time, the amount of time needed for a tablet to completely disintegrate in, e.g., a test subject's stomach or in isolated gastric juice, is measured. Alternatively, simulated body fluids can be used, such as simulated gastric juices.

Testing for Dissolution Rate in Gastric Fluids

The invention provides for isoflavone plant extract-containing compressed tablets that can dissolve in a gastric fluid within at least about 30 minutes and at least about 15 minutes. A variety of in vivo and in vitro means to evaluate and predict the dissolution behavior/dissolving rate of the tablets of the invention in the human stomach, i.e., in gastric fluid, are available.

For example, means to use "simulated" gastric fluid having substantially the same properties as fluids found in the stomach are well known in the art, see, e.g., Huang (1999) *Pharm Dev Technol* 4:107–115; Lee (1998) *Arch Pharm Res* 21:645–650; Abu-Izza (1998) *Pharm Dev Technol* 3:495–501; Galia (1998) *Pharm Res* 15:698–705.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The following examples are offered to illustrate, but not to limit the claimed invention.

Example 1

Manufacture of Isoflavone Plant Extract-Containing Tablets by Direct Compression Process The following example details exemplary means to manufacture the tablets of the invention, i.e., isoflavone plant extract-containing pressed tablets, by direct compression ("dry blend") manufacturing techniques.

First Exemplary Tablet and Method

Core Tablets

In this exemplary direct compression ("dry blend") manufacturing process of the invention, 61 parts of isoflavone plant extract (from a soy plant) (Indena, Seattle, Wash.) is mixed with 21 parts of water insoluble Emcosoy® soy polysaccharide, 13 parts of microcrystalline cellulose and 2 parts of silica gel. The mixture is milled through a 12-mesh screen and mixed with 2 parts of micronized stearic acid. The mixture is pressed on a rotary laboratory scale tablet press at press speed of 56 RPM. Each tablet has a weight on the average of about 706 mg, is oval in shape, and has a length of about 19 mm and a width of about 9 mm. The hardness of core tablets is about 11 Kp (determined using standard techniques, as discussed above).

The micronized stearic acid is unique to this invention for the successful manufacture of soy isoflavone plant extract-containing tablets using a direct compression process. Other pharmaceutical lubricants such as magnesium stearate, stearic acid (regular grade) or hydrogenated vegetable oil or triglycerides cannot replace micronized stearic acid as a lubricant in a problem-free compression process. Use of no or alternative lubricants known in the art in pressed isoflavone plant extract-containing tablets will result in an unacceptable product, with problems that include delamination, picking or sticking. Thus, the invention provides a solution to produce tablets containing isoflavone plant extracts with satisfactory characteristics (i.e. adequate hardness and reasonable disintegration time).

Water-insoluble polysaccharides serve, in part, as disintegrants in the formulation. In this invention, they were included in the formulation at unusually high levels (higher than standard manufacturing practice and higher than recommended by the supplier (in one embodiment, water-insoluble polysaccharide is Emcosoy®; its supplier is Penwest Pharmaceuticals, Patterson, N.Y.).

Coating of Tablets

In an alternative embodiment, the invention provides for the coating of pressed core tablets. In one exemplary procedure, core tablets are coated with an aqueous dispersion of hydroxypropyl methylcellulose, polyethylene glycol, titanium dioxide and a colorant. The coated tablets weigh 725 mg. They disintegrated in less than 21 minutes in a simulated gastric juice solution, as made and tested using standard United States Pharmacopia (USP) protocols. The disintegration method used simulated gastric fluid (as in USP) without pepsin.

Second Exemplary Tablet and Method

Core Tablets

In this exemplary direct compression ("dry blend") manufacturing process of the invention, 53 parts of the isoflavone soy extract is mixed with 21 parts of Emcosoy®, 21 parts of microcrystalline cellulose and 2 parts of silica gel. The mixture is milled through a 30-mesh screen and mixed with 2 parts of micronized stearic acid. The mixture is then pressed on a double sided 45-station rotary press at press speed of 2400 tablets per minute (TPM). The resultant core tablet weighs 695 mg, is oval, has a length of about 19 mm and a width of about 9 mm. The hardness of core tablets is about 19 Kp, measured using any of the techniques, discussed above.

The batch size in this example is about 200 Kg. This direct compression formulation and manufacturing process is capable of a commercial scale production for tablets containing soy isoflavone extract or other isoflavone-containing plant extract or glucoside-containing material.

Coating of Tablets

In an alternative embodiment, the invention provides for the coating of pressed core tablets. In one exemplary procedure, core tablets are coated with an aqueous dispersion of hydroxypropyl methylcellulose, polyethylene glycol, and maltodextrin. The coated tablets weigh on the average about 718 mg. They disintegrated in less than about 15 minutes in a simulated gastric juice solution, as made and tested using standard USP protocols, as discussed above (in a simulated gastric fluid without pepsin).

Third Exemplary Tablet and Method

Core Tablets

In this exemplary direct compression ("dry blend") manufacturing process of the invention, 58 parts of isoflavone soy extract is mixed with 21 parts of Emcosoy®, 17 parts of microcrystalline cellulose and 2 parts of silica gel. The mixture is milled through a 30-mesh screen and mixed with 2 parts of micronized stearic acid. The mixture is pressed on a double sided 45-station rotary press at press speed of 2400 TPM. The resultant tablets weigh about 699 mg, are oval, have a length of about 19 mm and a width of about 9 mm. The hardness of these core tablets is about 19 Kp.

The batch size in this example is about 400 Kg, which was a scale-up from the 200 Kg process described in the second exemplary tablet and method, above. Thus, this example describes a direct compression formulation and process that is capable of a commercial scale production for tablets containing soy isoflavone extract or other isoflavone-containing plant extract or other glucoside-containing materials.

Coating of Tablets

In an alternative embodiment, the invention provides for the coating of pressed core tablets. In one exemplary procedure, core tablets are coated with an aqueous dispersion of hydroxypropyl methylcellulose, polyethylene glycol, and maltodextrin. The coated tablets weigh on the average 721 mg. They disintegrated in less than about 15 minutes in a simulated gastric juice solution, as made and tested using standard USP protocols, as discussed above (in a simulated gastric fluid without pepsin).

Fourth Exemplary Tablet and Method

Core Tablets: In this exemplary direct compression manufacturing process of the invention, the following formulation for direct compression batch was used:

| Raw Material | Mg/tablet | % Formula |
|---|---|---|
| Soybean Isoflavone Extract (Indena, Seattle, WA) | 429.0 | 60.7 |
| Soy Polysaccharides (Emcosoy ®) | 156.0 | 22.0 |
| Microcrystalline Cellulose | 101.0 | 14.3 |
| Silica Gel | 7.0 | 1.0 |
| Magnesium Stearate | 7.0 | 1.0 |
| Glyceryl Behenate | 7.0 | 1.0 |
| Total | 707.0 | 100.0 |

The mixture of ingredients (except magnesium stearate and glyceryl behenate) from the above table is milled through a 20-mesh screen and mixed with 1 part each of magnesium stearate and glyceryl behenate. The mixture is pressed to 707 mg weight oval tablets having a length of 19 mm and a width of 9 mm on a rotary laboratory scale tablet press, such as Stokes 16-station press. The hardness of these core tablets is about 19 Kp. The disintegration of tablets was less than (<) 16 min. using the USP disintegration method in a simulated gastric fluid without pepsin. Cracking was observed but no delamination was seen on these tablets.

This example demonstrates that the water-insoluble polysaccharide (e.g., Emcosoy® at high usage level (about 22% by weight) resulted in a disintegration time of less than 16 min. for these isoflavone-containing tablets. As noted above, this amount of water-insoluble polysaccharide is novel to the invention, as it is greater than accepted manufacturing practice; the supplier-recommended usage level for Emcosoy® soy polysaccharides in tablets is only 4% to 10%.

The use of glyceryl behenate (1%) alone in direct compression could not provide adequate lubrication to the blend. The addition of 1% magnesium stearate to the blend containing 1% glyceryl behenate eliminated delamination, however unacceptable cracking remained on the tablets.

Fifth Exemplary Tablet and Method

Core Tablets

In this exemplary direct compression ("dry blend") manufacturing process of the invention, the following formulation for direct compression batch was used:

| Raw Material | Mg/tablet | % Formula |
|---|---|---|
| Soybean Isoflavone Extract (Indena, Seattle, WA) | 428.6 | 61.2 |
| Soy Polysaccharides (Emcosoy ®) | 100.2 | 14.3 |
| Microcrystalline Cellulose | 143.2 | 20.5 |
| Silica Gel | 14.0 | 2.0 |
| Micronized Stearic Acid (Tri Star) | 14.0 | 2.0 |
| Total | 700.0 | 100.0 |

The mixture of ingredients (except micronized stearic acid) from the above table is milled through a 14-mesh screen and mixed with 2 parts of micronized stearic acid. The mixture is pressed to 700 mg weight caplets having a length of 16 mm and a width of 7 mm on a rotary laboratory scale tablet press. The hardness of core tablets is about 16 Kp. The disintegration of tablets was 20 to 25 min. using the USP disintegration method in a simulated gastric fluid without pepsin. There was no cracking or delamination on these tablets.

This example demonstrated that the water-insoluble (soy) polysaccharide at a high usage level (14%) resulted in disintegration time of less than 25 min. for these isoflavone-containing tablets. As noted above, the supplier recommended usage level for this soy polysaccharides is 4–10%. The use of micronized stearic acid at a level of two percent (2%) provided adequate lubrication to the blend in the direct compression step and eliminated delamination and cracking on tablets.

Inadequate Manufacturing Method

Core Tablets

This example is provided to illustrate that without use of the novel methods of the invention, conventional direct compression ("dry blend") manufacturing processes are inadequate and cannot be used to make a pressed tablet containing isoflavone plant extract.

Formulation for exemplary direct compression batch

| Raw Material | Mg/tablet | % Formula |
|---|---|---|
| Soybean Isoflavone Extract (Indena, Seattle, WA) | 429.0 | 66.0 |
| Microcrystalline Cellulose | 170.3 | 26.2 |
| Croscarmellose Sodium | 32.5 | 5.0 |
| Silica Gel | 13.0 | 2.0 |
| Magnesium Stearate | 5.2 | 0.8 |
| Total | 650.0 | 100.0 |

The mixture of ingredients (except magnesium stearate) from the above table is milled through a 20-mesh screen and mixed with 0.8 parts of magnesium stearate. The mixture is pressed to 650 mg weight oval tablets having a length of 19 mm and a width of 9 mm on a rotary laboratory scale tablet press such as Stokes 16-station press. The hardness of core tablets is about 16 Kp. The disintegration of tablets was greater than (>) 30 min. using the USP disintegration method in a simulated gastric fluid without pepsin. Cracking and delamination were observed on these tablets.

This example demonstrates that the super-disintegrant croscarmellose sodium at a normal usage level (0.5–5%) could not provide enough disintegration property to isoflavone-containing tablets to manufacture a useable tablet, i.e., an isoflavone tablet that dissolves in gastric fluids in less than about 30 minutes. Additionally, magnesium stearate was not a good choice of lubricant for these isoflavone-containing tablets because it caused compression problems.

An additional exemplary core tablet formulation for direct compression is:

| Raw Material | Mg/tablet | % Formula |
|---|---|---|
| Soybean Isoflavone Extract (Indena, Seattle, WA) | 429.0 | 66.0 |
| Microcrystalline Cellulose | 72.8 | 11.2 |
| Croscarmellose Sodium | 130.0 | 20.0 |
| Silica Gel | 13.0 | 2.0 |
| Magnesium Stearate | 5.2 | 0.8 |
| Total | 650.0 | 100.0 |

The mixture of ingredients (except magnesium stearate) from the above table is milled through a 20-mesh screen and mixed with 0.8 parts of magnesium stearate. The mixture is pressed to 650 mg weight oval tablets having a length of 19 mm and a width of 9 mm on a rotary laboratory scale tablet press such as Stokes 16-station press. The hardness of core tablets is about 16 Kp. The disintegration of tablets was 22–25 min. using the USP disintegration method in a simulated gastric fluid without pepsin. Cracking and delamination were observed on these tablets.

This example demonstrates that the super-disintegrant croscarmellose sodium at unusually high usage level (20%) was still not enough to make isoflavone-containing tablets disintegrate within 20 min. Furthermore, magnesium stearate is not a good choice of lubricant for isoflavone-containing tablets, for it caused significant compression problems, resulting in unacceptable cracking and delamination.

Example 2

Manufacture of Isoflavone-Containing Tablets by Granulation Process

The following example details exemplary means to manufacture the tablets of the invention, i.e., isoflavone-containing pressed tablets, by granulation manufacturing techniques.

Core Tablets

In this exemplary granulation manufacturing process of the invention, 61 parts of isoflavone plant extract (from a soy plant) is mixed with 22 parts of Emcosoy® soy polysaccharide. The mixture is granulated in a fluidized bed processor (by top-spray) using a solution of 0.6 parts of Hydroxypropyl Methylcellulose and 20 parts of water. The resulting granules are dried. The granules are sieved and mixed with 15 parts of Microcrystalline Cellulose and 1 part of Glyceryl Behenate. The mixture is then pressed on a rotary laboratory scale tablet press. The resultant core tablet is 708 mg in weight and oval, having a length of 19 mm and a width of 9 mm. The hardness of these core tablets is about 15 Kp.

The above described granulation process is one solution to produce tablets containing isoflavone-containing plant extract using a rotary tablet press to manufacture a tablet with satisfactory characteristics (i.e. adequate hardness and reasonable disintegration time). The unique excipient in the formulation is a water-insoluble polysaccharide, e.g., from soy, e.g., Emcosoy® (supplier: Penwest Pharmaceuticals, Patterson, N.Y.). The water-insoluble polysaccharide serves, in part, as a disintegrant. As noted above, it was included in the formulation at an unusually high level, as discussed above.

Coating of Tablets

In an alternative embodiment, the invention provides for the coating of pressed core tablets. In one exemplary procedure, core tablets are coated with an aqueous dispersion of hydroxypropyl methylcellulose, polyethylene glycol, titanium dioxide and a colorant. The coated tablets weigh 719 mg. They disintegrated in less than 10 minutes in a simulated gastric juice solution, as made and tested using standard USP protocols (as discussed above).

Example 3

Coating Isoflavone-Containing Tablets of the Invention

The following example details exemplary means to manufacture coated tablets of the invention.

The coating material Opadry® II Clear from Colorcon (West Point, Pa.) was used; it contains hydroxypropyl methylcellulose, polyethylene glycol and maltodextrin. The dry powder of Opadry® II Clear was dispersed in purified water to form a 10% to 15% (weight-by-weight) film coating dispersion.

The isoflavone-containing core tablets of the invention were successfully coated with this water-based coating system under the following coating conditions (otherwise, all materials and apparatus and manufacturing techniques were conventional in the art):

| Coating Parameters | Range |
|---|---|
| Supply Air Temperature during Spray | 45–55° C. |
| Exhaust Air Temperature during Spray | 30–37° C. |
| Solution Spray Rate | 670–730 ml/min |
| Supply Air Flow Rate | 2950–3450 SCFM |
| Atomizing Air Pressure | 38–42 PSI |

What is claimed is:

1. A direct compression process for producing a tablet comprising the following steps:
   (a) mixing an initial formulation comprising
       an isoflavone-containing plant extract,
       a water-insoluble polysaccharide, wherein the amount of the water-insoluble polysaccharide in the tablet comprises at least about 15% of the dry weight of the tablet,
       a filler, and
       a silica gel glidant wherein the amount of the silica gel in the tablet comprises between about 1% to about 5% of the dry weight of the tablet;
   (b) milling the mixed formulation;
   (c) mixing into the milled and mixed formulation a micronized stearic acid, wherein the amount of the micronized stearic acid in the tablet comprises between about 1% to about 5% of the dry weight of the tablet; and
   (d) pressing the milled formulation into a tablet form, wherein the compression force of the press on the tablet is at least about 15 kilopounds.

2. The direct compression process of claim 1, wherein the isoflavone-containing plant extract is from the fruit of a Leguminosae family plant.

3. The direct compression process of claim 2, wherein the fruit is a soy bean.

4. The direct compression process of claim 1, wherein the compression force of the press on the tablet is between about 17 to about 23 kilopounds.

5. The direct compression process of claim 1 further comprises a coating process comprising the following steps:
   (a) coating the pressed tablets with an aqueous dispersion comprising a cellulose-based polymer; and
   (b) drying the coated tablets, wherein the drying does not heat the tablet more than about 40° C.

6. The method of claim 1, wherein the water-insoluble polysaccharide is a plant water-insoluble polysaccharide.

7. The method wherein the plant water-insoluble polysaccharide is a soybean plant water-insoluble polysaccharide.

8. The method of claim 7, wherein the soybean plant water-insoluble polysaccharide includes cellulose, hemicellulose, pectin, gum and mucilage.

9. The method of claim 1, wherein the amount of the water-insoluble polysaccharide in the tablet comprises between about 15% to about 25% of the dry weight of the tablet.

10. The method of claim 1, wherein the amount of the water-insoluble polysaccharide in the tablet comprises about 21% to 22% of the dry weight of the tablet.

11. The method of claim 1, wherein the amount of the isoflavone-containing plant extract in the tablet comprises between about 10% to about 85% of the dry weight of the tablet.

12. The tablet method of claim 11, wherein the amount of the isoflavone-containing plant extract in the tablet comprises between about 25% to about 70% of the dry weight of the tablet.

13. The method of claim 12, wherein the amount of the isoflavone-containing plant extract in the tablet comprises about 45% to about 65% of the dry weight of the tablet.

14. The method of claim 1, wherein the tablet can disintegrate in a gastric fluid within at least about 30 minutes.

15. The method of claim 1, wherein the tablet further comprises a micronized fatty acid in an amount between about 1% to about 5% of the dry weight of the tablet.

16. The method of claim 15, wherein the amount of the micronized fatty acid in the tablet comprises about 2% of the dry weight of the tablet.

17. The method of claim 15, wherein the micronized fatty acid is a micronized stearic acid.

18. The method of claim 1, wherein the amount of the silica gel in the tablet comprises about 2% of the dry weight of the tablet.

19. The method of claim 1, wherein the tablet is suitable for delivery to a body cavity of the group consisting of the oral, buccal, sublingual, vaginal or rectal cavities.

20. The method of claim 1, wherein the formulation further comprises at least one additive agent selected from the group consisting of a disintegrant, a flavorant, an artificial sweetener, a perfume, and a colorant.

* * * * *

UNITED STATES PATENT AND TRADEMARK OFFICE
CERTIFICATE OF CORRECTION

PATENT NO.    : 6,669,956 B2
DATED         : December 30, 2003
INVENTOR(S)   : He et al.

It is certified that error appears in the above-identified patent and that said Letters Patent is hereby corrected as shown below:

<u>Title page,</u>
Item [54], Title, insert -- NOVEL -- before "TABLETS".

<u>Column 20,</u>
Line 64, delete "tablet" after "The".

Signed and Sealed this

Sixth Day of April, 2004

JON W. DUDAS
*Acting Director of the United States Patent and Trademark Office*